US007846905B2

(12) United States Patent
Tanaka et al.

(10) Patent No.: US 7,846,905 B2
(45) Date of Patent: Dec. 7, 2010

(54) AGENT FOR INHIBITING VISCERAL FAT ACCUMULATION

(75) Inventors: Miyuki Tanaka, Zama (JP); Eriko Misawa, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 0 days.

(21) Appl. No.: 11/913,022

(22) PCT Filed: Sep. 21, 2006

(86) PCT No.: PCT/JP2006/318685

§ 371 (c)(1),
(2), (4) Date: Oct. 29, 2007

(87) PCT Pub. No.: WO2007/034851

PCT Pub. Date: Mar. 29, 2007

(65) Prior Publication Data

US 2009/0069254 A1    Mar. 12, 2009

(30) Foreign Application Priority Data

Sep. 22, 2005 (JP) ............................. 2005-275171
Sep. 30, 2005 (JP) ............................. 2005-287887

(51) Int. Cl.
*A01N 45/00* (2006.01)
*A61K 9/00* (2006.01)
*A61K 36/00* (2006.01)
(52) U.S. Cl. .......................... 514/26; 424/725; 424/400
(58) Field of Classification Search ...................... None
See application file for complete search history.

(56) References Cited

U.S. PATENT DOCUMENTS

| 4,735,935 A | 4/1988 | McAnalley |
| 6,280,751 B1 | 8/2001 | Fletcher et al. |
| 6,506,387 B1 * | 1/2003 | Cohen ......................... 424/744 |
| 2006/0116333 A1 * | 6/2006 | Komeda et al. ............... 514/27 |
| 2008/0194492 A1 * | 8/2008 | Brenneisen et al. ........... 514/19 |

FOREIGN PATENT DOCUMENTS

| JP | 05-170651 | 7/1993 |
| JP | 07-165587 | 6/1995 |
| JP | 10-036283 | 2/1998 |
| JP | 11-193296 | 7/1999 |
| JP | 2000-319190 | 11/2000 |
| JP | 2001-240544 | 9/2001 |
| JP | 2003-286185 | 10/2003 |
| JP | 2005-015425 | 1/2005 |
| NZ | 330439 | 12/2000 |
| WO | WO 2004/105770 | 12/2004 |
| WO | WO 2005/095436 | 10/2005 |
| WO | WO 2006/123464 | 11/2006 |
| WO | WO 2006/123465 | 11/2006 |

OTHER PUBLICATIONS

Panosyan, et al. "Sterols and Sterol Glycosides of Bryonia alba," *Khimiya Prirodnykh Soedinenii*, No. 3, pp. 353-360, 1977.
International Search Report dated Dec. 18, 2006.
Igaku to Seibutsugaku, vol. 125, No. 5, pp. 189-194, Nov. 10, 1992.
Journal of Medicine of Fujita Gakuen, vol. 22, No. 2, pp. 153-157, 1998.
Muravyova, "Tropical and Subtropical Mediccinal Plants," *Medicine*, Third edition, revised and supplemented, pp. 285-288, 1997.
Office action issued Jan. 19, 2009 in a corresponding Russian counterpart application.
Mohammad Kabiruddin; Bayaaz-e-Kabir, vol. II (compiled), Daftar-al-Maseeh, Karol Bagh, New Delhi, 1938, p. 36.
Dundukanatha; Rasendracintamanaih Trans. Siddhinandan Mishra, Chaukhamba Orientalia (Varanasi) Ed. $1^{st}$ 1999, p. 348.
Rasatantrasarah Evam Siddhaprayogasamgrahah; Part I: Krishan Gopal Ayurveda Bhawan; Edn. $8^{th}$; 1990, pp. 266-267 (This book contains back references from 1000 BC to $20^{th}$ century).
Rasayoga Sagara-Compiled and translated by Vaidya Pandita Hariprapanna Ji, vol. II: Krishnadas Academy, Varanasi, Edn. Reprint, 1998, p. 561 (This book contains back references from 1000 BC to $20^{th}$ century).
Rasayoga Sagara-Compiled and translated by Vaidya Pandita Hariprapanna Ji, Vol. II: Krishnadas Academy, Varanasi, Edn. Reprint, 1998, p. 213 (This book contains back references from 1000 BC to $20^{th}$ century).
Nityanathasiddhah; Rasaratnakarah-Rasendra Khandam Comm. Datto Vallal Borakara, Ed. $2^{nd}$, 1986, Shri Gajanau Book Depot (Pune), pp. 387-389.
Cudamani; Rasakamadhenu Samhita-Edited by Jiraramakalidasa Sastri, Part 4, Chaukhambha Publishers, Varanasi, Edn. $1^{st}$, 1992, p. 382.
Communication from European Patent Office issued to application No. 06810359.7-2112/1927361, dated Jul. 30, 2010 with Annexes 1-3.

* cited by examiner

*Primary Examiner*—Christopher R Tate
*Assistant Examiner*—Randall Winston
(74) *Attorney, Agent, or Firm*—Knobbe, Martens, Olson & Bear, LLP

(57) ABSTRACT

To reduce amounts of fat accumulated in abdominal cavity and to prevent or ameliorate visceral fat type obesity considered to be a main factor of metabolic syndrome, there is provided an agent or a food or drink, including as an active ingredient 3-O-β-D-glucopyranosyl-4-methylergost-7-en-3-ol, an organic solvent extract, a hot water extract, a squeezed liquid of a Liliaceae plant or a fraction thereof which contains the compound.

1 Claim, No Drawings

AGENT FOR INHIBITING VISCERAL FAT ACCUMULATION

RELATED APPLICATIONS

This application is the U.S. National Phase under 35 U.S.C. §371 of International Application PCT/JP2006/318685, filed Sep. 21, 2006, which was published in a non-English language, which claims priority to JP Application No. 2005-275171, filed Sep. 22, 2005 and JP 2005-287887, filed Sep. 30, 2005.

TECHNICAL FIELD

The present invention relates to an agent for inhibiting visceral fat accumulation, which contains 3-O-β-D-glucopyranosyl-4-methylergost-7-en-3-ol as an active ingredient, and a food or drink containing the same. In particular, the present invention relates to an agent for inhibiting visceral fat accumulation, which is capable of decreasing an amount of fat accumulated in abdominal cavity and preventing or improving visceral fat type obesity which is considered to be a main factor of metabolic syndrome, and relates to a physiologically functional food or drink containing the same, such as a food for specified health use.

BACKGROUND ART

In recent years, a rapid increase in obesity involved in westernization of lifestyle has become a serious problem. The obesity means a state in which excessive energy is accumulated because of excessive ingestion of calories and a decrease in calorie consumption caused by insufficient exercise or the like, and is "state in which excessive amount of fat tissues of a body (body fat) is accumulated". It has been indicated that the obesity can be a basis of onset of so-called lifestyle-related diseases such as diabetes, hypertension and hyperlipidemia and so forth.

The obesity exhibits a state of accumulation of excessive body fat and a phenomenon of body weight increase. It is reported that, when rapid decrease of body weight is conducted to improve obesity, amounts of muscles essential for energy consumption are also decrease together with the fat, and in a case of elders, symptoms such as blood pressure disorder and injury of articulatio coxae may occur (Non-patent Document 1). Furthermore, there is a report on an exercise therapy which is expected to exert an effect of improving muscle tissues in a case where decrease of the amount of fat is conducted without reducing a body weight (Non-patent Document 2). As described above, in recent years, methods of improving obesity by inhibiting accumulation of body fat instead of merely decreasing body weight have been attracting attention.

The fat tissues are grouped into subcutaneous fat which is accumulated inside of a skin and visceral fat which is accumulated around visceral organs in an abdominal cavity, which are collectively called "body fat". It is known that obesity is classified into groups of: subcutaneous fat type obesity involving accumulation of the subcutaneous fat; and visceral fat type obesity involving the visceral fat accumulation. The visceral fat accumulation particularly gives large effects on frequency of onset of complications such as abnormal metabolism and cardiovascular diseases and severity thereof in obesity.

Conventionally, it is known that pathosis in which an individual is suffering from a combination of a plurality of lifestyle-related diseases, that is, "multiple risk factor syndrome", significantly increases the risks of onset of arteriosclerotic disease, and concepts that Syndrome X and metabolic syndrome is risk factors of arteriosclerosis have been proposed. Because of the proposal of those multiple risk factor syndromes, in order to achieve more comprehensive risk evaluation and to prevent the onset of arteriosclerosis, international integration of definition of metabolic syndrome and diagnostic criteria therefore were conducted (Non-patent Document 3). In the diagnostic criteria for metabolic syndrome which was proposed in Japan in April, 2005, a waist size corresponding to a visceral fat area of 100 $cm^2$ or more is adopted as an essential item instead of a body mass index (BMI) or a body fat percentage which is generally used for indicating a level of obesity. Thus, the visceral fat accumulation has been recognized to be largely involved in the cause of the metabolic syndrome.

Exercise, diet and behavior therapies are recommended as means for decreasing body fat. However, in a case where those therapies are difficult to be carried out or continued, drug therapy or a surgery may be conducted. At present, mazindol that is an anorectic is used as a therapeutic drug for obesity, and is basically prescribed only for person suffering from high levels of obesity which show BMI of 35 or more. However, mazindol not only gives side effects such as headache and dry mouth, but also has a large number of problems in that mazindol has contraindication when severe dysfunctions are present in the kidney, liver or pancreas, and cannot be administered for a long period of time because of its dependency, and the like.

Plant sterols such as β-sitosterol, campesterol, stigmasterol have already been known to have a reducing effect on blood cholesterol by inhibiting absorption of the cholesterol, and there is disclosed a lipid metabolism-improving agent containing diglyceride and plant sterol as active ingredients (Patent Document 1). Further, there are disclosed an anti-obesity agent and a lipid metabolism-improving agent containing a cholestenone compound synthesized by using the plant sterols such as β-sitosterol and campesterol as a starting material, or 4-cholesten-3-one (Patent Documents 2 to 5) as an active ingredient.

The genus *Aloe* belonging to Liliaceae plant is a group of plants including *Aloe vera* (*Aloe barbadenisis* Miller), *Aloe arborescens* (*Aloe arborescens* Miller var. *natalensis* Berger) as a typical plant, and they are known to have various efficacies. Specifically, it is disclosed that an *Aloe* extract has a preventive or improving effect on obesity (Patent Document 6). In addition, there are disclosed a supplement having an effect of decreasing a body weight which contains 0.25% of *Aloe vera* powder (Patent Document 7) and an essential oil composition for controlling body weight which contains *Aloe vera* (Patent Document 8). Furthermore, it is reported that administration of a whole leaf of *Aloe arborescens* to a rat significantly decreased body weight depending on concentrations of *Aloe arborescens* (Non-patent Document 4 or 5).

[Patent Document 1] Japanese Patent Laid-open No. 2005-15425

[Patent Document 2] Japanese Patent Laid-open No. 07-165587

[Patent Document 3] Japanese Patent Laid-open No. 11-193296

[Patent Document 4] Japanese Patent Laid-open No. 2001-240544

[Patent Document 5] Japanese Patent Laid-open No. 05-170651

[Patent Document 6] Japanese Patent Laid-open No. 2000-319190

[Patent Document 7] New Zealand Patent No. 330439

[Patent Document 8] U.S. Pat. No. 6,280,751

[Non-patent Document 1] Journal of Applied Physiology, vol. 95, 2003, pp. 1728-1736

[Non-patent Document 2] Journal of Applied Physiology, vol. 99, 2005, pp. 1220-1225

[Non-patent Document 3] Adiposcience, vol. 2, 2005, pp. 11-15

[Non-patent Document 4] Igaku to Seibutsugaku, vol. 125, No. 5, pp. 189-194

[Non-patent Document 5] Journal of Medicine of Fujita Gakuen, vol. 22, No. 2, pp. 153-157

DISCLOSURE OF THE INVENTION

Patent Document 1 does not describe an effect of administration of plant sterol alone, and does not describe or suggest the effect of the plant sterol on visceral fat.

In addition, there are disclosed that the 3-ketosteroid compound disclosed in Patent Document 2, the cholestenone compound disclosed in Patent Document 3 and 24-alkylcholesten-3-one compounds such as 24-methylcholest-5-en-3-one disclosed in Patent Document 4 have effects of decreasing body weight, an amount of body fat, and an amount of blood lipid. However, there is no description or suggestion that the compounds have an effect of inhibiting visceral fat accumulation without affecting an amount of oral ingestion and an increase in body weight.

4-cholesten-3-one disclosed in Patent Document 5 is apparently different from the active ingredient of the present invention. Specifically, the effect of 4-cholesten-3-one described in Patent Document 5 is that, when a normal mouse ingests calories, the compound decreases an excessive amount of fat in an abdominal cavity together with fat components regarded to be within a normal range more than necessary. Therefore, the effect of 4-cholesten-3-one described in Patent Document 5 is clearly different from the effect of the present invention of effectively inhibiting only the fat components accumulated around visceral organs in an amount more than necessary in a case of an obese state or in a case where excessive amounts of calories are ingested.

Furthermore, it is disclosed that the agent for preventing and improving obesity of Patent Document 6 inhibits progression of obesity involving an increase in body weight, and thus is effective for maintaining a standard body weight without necessitating excessive diet restriction. However, there is no description on the effect on the body fat, and no description is made on the effect of inhibiting visceral fat accumulation, by which the amount of visceral fat is decreased without a decrease in body weight.

In addition, the active ingredient described in Patent Document 6 is an *Aloe* extract. However, components related to the inhibition of the progression of obesity involving an increase in body weight are not specified at all. Therefore, it has been difficult to predict from the description of Patent Document 6, the effect of inhibiting visceral fat accumulation, which is different from the effect of Patent Document 6 and can decrease the visceral fat without decrease in body weight, and the presence of the effect.

Accordingly, with regard to an agent capable of selectively reducing the visceral fat which is strongly related to onset of metabolic syndrome, or capable of preventing and inhibiting accumulation thereof, there has been demanded a further development of a functional material which can be ingested daily safely with pain as little as possible, and can efficiently reduce the visceral fat.

In view of the aforementioned problems, the inventors of the present invention assiduously studied on an agent for inhibiting visceral fat accumulation, which can prevent or improve visceral fat type obesity that is considered to be a main cause of metabolic syndrome. As a result, the inventors of the present invention have found that 3-O-β-D-glucopyranosyl-4-methylergost-7-en-3-ol has an effect of efficiently decreasing fat accumulated in an abdominal cavity. In addition, it was found that the effect can maintain a standard body weight without a decrease in body weight, and thus is useful for inhibiting progression of obesity without necessitating excessive diet restriction.

An object of the present invention is to provide an agent for inhibiting visceral fat accumulation, which contains 3-O-β-D-glucopyranosyl-4-methylergost-7-en-3-ol as an active ingredient. In addition, another object of the present invention is to provide a physiologically functional food or drink containing the agent for inhibiting visceral fat accumulation, such as a food for specified health use.

First invention of the present application to solve the aforementioned problems is an agent for inhibiting visceral fat accumulation containing a compound represented by the following chemical formula (1) as an active ingredient.

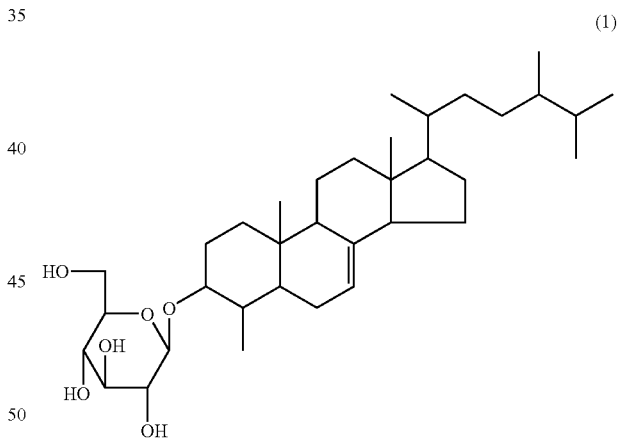

(1)

Second invention of the present application to solve the aforementioned problems is an agent for inhibiting visceral fat accumulation, which contains an organic solvent extract, hot water extract or squeezed liquid of a plant containing a compound represented by the following chemical formula (1), or a fraction thereof as an active ingredient, wherein the organic solvent extract, hot water extract or squeezed liquid of the aforementioned plant, or the fraction thereof contains at least 0.001% by dry mass of a compound represented by the following chemical formula (1). Furthermore, it is preferred that the aforementioned plant is a Liliaceae plant.

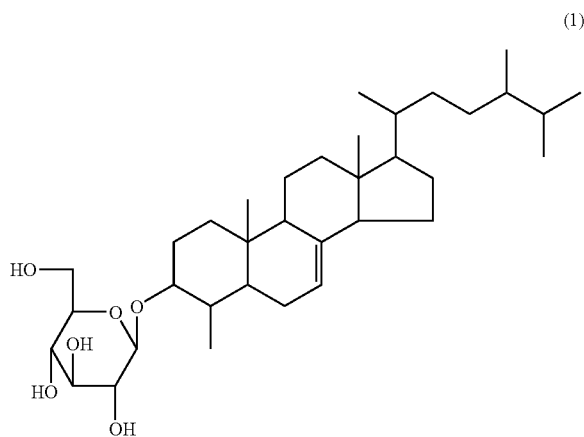

(1)

Third invention of the present application to solve the aforementioned problems is a food or drink containing the agent for inhibiting visceral fat accumulation according to the first or second invention, wherein it is preferred that the food or drink contains 0.0001% by dry mass or more of the compound represented by the aforementioned chemical formula (1).

Fourth invention of the present application to solve the aforementioned problems is use of a compound represented by the aforementioned chemical formula (1), or an organic solvent extract, hot water extract or squeezed liquid of a plant containing at least 0.001% by dry mass of the compound, or a fraction thereof, in the production of an agent for inhibiting visceral fat accumulation. Furthermore, it is preferred that the aforementioned plant is a Liliaceae plant.

Fifth invention of the present application to solve the aforementioned problems is a method for inhibiting visceral fat accumulation, which comprises administering a compound represented by the aforementioned chemical formula (1), or an organic solvent extract, hot water extract or squeezed liquid of a plant containing at least 0.001% by dry mass of the compound, or a fraction thereof to a subject whose visceral fat accumulation is to be inhibited. Furthermore, it is preferred that the aforementioned plant is a Liliaceae plant.

The agent for inhibiting visceral fat accumulation of the present invention and the food or drink containing the same can be safely administered or ingested, and have effects of efficiently inhibiting visceral fat accumulation. Furthermore, the active ingredient of the agent for inhibiting visceral fat accumulation of the present invention can be produced easily from a plant of the family Liliaceae such as *Aloe vera* (*Aloe barbadensis* Miller) that can be safely ingested from an experiential viewpoint for food and is readily available.

BEST MODE FOR CARRYING OUT THE INVENTION

Hereafter, preferred embodiments of the present invention will be explained in detail. However, the present invention is not limited to the following preferred embodiments and can be freely modified within the scope of the present invention. In addition, percentage as used herein indicates mass unless otherwise specified.

In the present invention, the effect of inhibiting visceral fat accumulation means an effect for decreasing an amount of fat accumulating in the abdominal cavity. Therefore, the effect of inhibiting visceral fat accumulation can be evaluated by measuring an amount of fat in the abdominal cavity such as a weight of mesenteric fat.

The compound used as the active ingredient of the agent for inhibiting visceral fat accumulation (hereinafter also referred to as "the agent of the present invention") of the present invention is the compound having the structure represented by the aforementioned chemical formula (1), that is, 3-O-β-D-glucopyranosyl-4-methylergost-7-en-3-ol. The compound of the present invention has a structure formed by dehydration condensation of the hydroxyl group at the 3-position of 4-methylergost-7-en-3-ol and the hydroxyl group at the 1-position of D-glucose.

Furthermore, the composition used as the active ingredient of the agent for inhibiting visceral fat accumulation of the present invention (hereinafter also referred to as "the composition of the present invention") is an extract of a plant of the family Liliaceae, or a fraction thereof containing at least 0.001% by dry mass, preferably 0.01% by dry mass or more, and more preferably 0.1% by dry mass or more of the aforementioned compound of the present invention. The upper limit of the content of the compound of the present invention is not particularly limited, and it may be, for example, preferably 10% by dry mass, or 50% by dry mass, 70% by dry mass or 90% by dry mass.

In the present invention, dry mass means a mass measured after a compound is dried by the drying method defined by "Drying Loss Test" that is a general test method as described in Japanese Pharmacopoeia, 14th Revision (Mar. 30, 2001, Japan Ministry of Health, Labor and Welfare, Ministerial Notification No. 111). For example, the mass of the compound of the present invention can be determined in such a manner that: about 1 g of the compound of the present invention is measured off, and dried at 105° C. for 4 hours; and the resultant is cooled by standing in a desiccator; and the mass of the compound is weighed with a scale.

The compound of the present invention or a composition containing the same can be produced by, for example, extracting a fraction containing the compound of the present invention from a plant belonging to the family Liliaceae and containing the compound of the present invention, a part thereof, or a disruption product thereof by using an organic solvent or hot water and concentrating the fraction.

Examples of the aforementioned plant belonging to the family Liliaceae include plants belonging to the genus *Aloe* or *Allium*. Examples of the plants of the genus *Aloe* include *Aloe barbadensis* Miller, *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferred to use mesophyll (clear gel portion) thereof. Such a plant or a part thereof is disrupted preferably by using a homogenizer or the like and thereby liquefied, and the compound of the present invention or a composition containing the same is extracted from the disruption product by using an organic solvent or hot water. Examples of the organic solvent include alcohols such as methanol, ethanol and butanol and so forth; esters such as methyl acetate, ethyl acetate, propyl acetate and butyl acetate and so forth; ketones such as acetone and methyl isobutyl ketone and so forth; ethers such as diethyl ether and petroleum ether and so forth; hydrocarbons such as hexane, cyclohexane, toluene and benzene and so forth; halogenated hydrocarbons such as carbon tetrachloride, dichloromethane and chloroform and so forth; heterocyclic compounds such as pyridine and so forth; glycols such as ethylene glycol and so forth; polyhydric alcohols such as polyethylene glycol and so forth; nitrile solvents such as acetonitrile and so forth, mixtures of these solvents and so forth. Furthermore, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature at or below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform: methanol=about 5:1. Furthermore, when a gradient of methanol/water mixture is used in reverse phase silica gel column chromatography as an elution solvent, the compound of the present invention is eluted with methanol of a concentration of about 95%. The obtained fraction can be further purified by HPLC or the like.

Whether the compound or composition containing the same obtained as described above actually contains the compound of the present invention can be confirmed by measuring the effect for inhibiting visceral fat accumulation as an indicator by using, for example, the methods shown in the examples described later. Whether the compound is a glycoside bound with glucose at the aglycon moiety, or whether the aglycon moiety is 4-methylergost-7-en-3-ol can be confirmed by, for example, $^{13}$C-NMR or the like.

The compound of the present invention can also be produced by condensing D-glucose and 4-methylergost-7-en-3-ol. 4-Methylergost-7-en-3-ol can be obtained by extracting from a plant and purifying it. D-Glucose and 4-methylergost-7-en-3-ol can be condensed by, for example, a combination of the methods described in Jikken Kagaku Koza (Lecture of Experimental Chemistry), 4th edition, vol. 26, 1992 (described in p. 272, p. 297 and p. 342). That is, D-glucose is completely acetylated, and then the anomeric position is converted to α-bromide. Then, 4-methylergost-7-en-3-ol is reacted with α-bromide in diethyl ether to attain β-glycosylation, and thereafter the acetyl group is hydrolyzed in a sodium methoxide/methanol mixture to obtain the objective compound.

The compound of the present invention can be used as an active ingredient of the agent for inhibiting visceral fat accumulation of the present invention and a food or drink containing the same as it is. Further, an organic solvent extract, a hot water extract or squeezed liquid of a plant containing the compound of the present invention, or a fraction thereof (hereinafter referred to as "extract etc.") may also be used as an active ingredient of the agent for inhibiting visceral fat accumulation and a food or drink containing the same.

In the present invention, the squeezed liquid can be obtained by processing a homogenate of a plant by a compressor, collecting a crude of squeezed liquid of a plant, and filtering the crude to eliminate insoluble fraction (contaminant) by filter or filter cloth. For example, when the *Aloe vera* is used as a plant of the family Liliaceae, *Aloe vera* squeezed liquid can be prepared by processing mesophyll gel portion obtained by hulling leaf of *Aloe vera* by a crusher, compressing a squeezed liquid to collect *Aloe vera* crude, and filtering the *Aloe vera* crude to eliminate contaminant by filter or filter cloth. In this case, it is preferred that total content of aloin and aloe-emodin, which are contained a lot in leaf-skin of *Aloe vera*, is 5 ppm or less.

The aforementioned extract etc. to be contained in the agent for inhibiting visceral fat accumulation preferably contains at least 0.001% by dry mass, more preferably 0.01 to 1% by dry mass, particularly preferably 0.05 to 1% by dry mass, of the compound of the present invention. Further, the aforementioned extract etc. to be contained in a food or drink preferably contains at least 0.0001% by dry mass, more preferably 0.001 to 1% by dry mass, particularly preferably 0.005 to 1% by dry mass, of the compound of the present invention. The aforementioned extract etc. may contain two or more types of the compound of the present invention. Further, the aforementioned extract etc. may be a solution, or can also be lyophilized or spray-dried in a conventional manner and stored or used as powder.

As the agent for inhibiting visceral fat accumulation of the present invention, the compound of the present invention or a composition containing the same such as extract etc. per se, or those combined with a pharmaceutically acceptable carrier can be orally or parenterally administered to a mammal including human. In the agent of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate and hydrobromate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the agent for inhibiting visceral fat accumulation of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual agent for inhibiting visceral fat accumulation as pharmaceutical carriers such as excipients, binders, disintegrating agents, lubricants, stabilizers, flavoring agents, diluents, surfactants and solvents for injection and so forth can be used. Further, so long as the effect of the present invention is not degraded, the compound of the present invention, or the extract etc. containing the same can be used in combination with other agents having an effect for inhibiting visceral fat accumulation.

Although the amount of the compound of the present invention or the extract etc. containing the same contained in the agent for inhibiting visceral fat accumulation of the present invention is not particularly limited and can be suitably selected, the amount may be, for example, at least 0.001% by mass, preferably 0.01 to 1% by mass, particularly preferably 0.05 to 1% by mass, in terms of the amount of the compound of the present invention.

The agent for inhibiting visceral fat accumulation of the present invention has the effect of inhibiting visceral fat accumulation, and thus can prevent the visceral fat type obesity. The visceral fat type obesity generally means a state where an area of visceral fat is 100 cm$^2$ or more, and according to the diagnostic criteria for metabolic syndrome, means a case in which a Japanese male has a waist size of 85 cm or more, or a Japanese female has a waist size of 90 cm or more (Internal Medicine, vol. 94, pp. 188-203, 2005). In addition, the agent for inhibiting visceral fat accumulation of the present invention is preferably used for treatment of a patient who has a larger amount of the visceral fat accumulated than a healthy person.

Furthermore, the agent for inhibiting visceral fat accumulation of the present invention can improve or prevent diseases, complications and the like caused by the visceral fat accumulation, such as abnormal lipid metabolism and cardiovascular diseases, and can also decrease risks of those diseases, complications and the like. Examples of the various diseases caused by the visceral fat accumulation include obesity, in particular, visceral fat type obesity, hyperlipidemia, diabetes, hypertension and arteriosclerosis. In addition, examples of the complications caused by those diseases include: diabetic retinopathy, nephropathy, neuropathy and diabetic gangrene caused by diabetes; cerebral embolism, nephrosclerosis and renal failure caused by hypertension; and cerebral embolism, cerebral infarction, cardiovascular diseases such as angina pectoris and cardiac infarction, and nephropathy such as uremia, nephrosclerosis and renal failure caused by arteriosclerosis.

Furthermore, the agent for inhibiting visceral fat accumulation of the present invention is useful for preventing onset of metabolic syndrome. The effect of the agent of inhibiting or decreasing visceral fat accumulation as described above is extremely effective for preventing the onset of metabolic syndrome and metabolic syndrome-related arteriosclerotic diseases, lifestyle-related diseases indicated as risk factors thereof such as diabetes, hypertension and hyperlipidemia, and complications associated with those diseases. In addition, metabolic syndrome in the present invention means states observed in multiple risk factor syndrome, that is, states where arteriosclerosis easily occur and in which such symptoms regarded as risk factors as hyperinsulinemia, abnormal glucose tolerance or hyperglycemia, abnormal lipid metabolism, hyperlipidemia (hypertriglyceridemia and hypo-HDL-cholesterolemia), hypertension, obesity and visceral fat accumulation. In addition, the inventors of the present invention have found that the compound of the present invention has an effect of decreasing hemoglobin A1c level and improving hyperglycemia (WO 2005/095436). It is preferred that the diseases to which the agent for inhibiting visceral fat accumulation of the present invention is applied are not accompanied with a state where the hemoglobin A1c level is higher than that of a healthy person.

The administration time of the agent of the present invention is not particularly limited and can be suitably selected according to the method for treating an objective disease. Furthermore, the administration route is preferably determined depending on the dosage form, age, sex and other conditions of patients, severity of symptoms of patients and so forth. The dose of the agent of the present invention is suitably selected depending on the dosing regimen, age, sex, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Further, when an extract etc. containing the compound of the present invention is used, the dry weight of the extract etc. is selected from the range of, preferably 0.1 to 1000 mg/kg/day, more preferably 1 to 100 mg/kg/day, as a tentative amount. In any case, the dose can be ingested, in a day, once or several times as divided portions.

The compound of the present invention or the composition containing the same can be added to food or drink (a drink or a food) to produce a food or drink having an effect of inhibiting visceral fat accumulation. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added. Furthermore, the amount of the compound of the present invention or the extract etc. containing the same contained in the food or drink of the present invention is not particularly limited and can be suitably selected. For example, the compound of the present invention or the extract etc. containing the same is contained in food or drink in an amount of at least 0.0001% by mass, preferably 0.001 to 1% by mass, particularly preferably 0.005 to 1% by mass, in terms of the amount of the compound of the present invention.

The food or drink of the present invention can be used to various applications utilizing the effect of decreasing visceral fat. For example, it can be used as food or drink suitable for a person who began to worry about their waist size, food or drink suitable for a person who began to worry about blood lipid, and food or drink useful for decreasing or eliminating risk factors of metabolic syndrome, and the like.

In the present invention, "inhibiting visceral fat accumulation" means an effect for improving or preventing various adverse effects on health caused by an visceral fat accumulation. "Improving visceral fat type obesity", "preventing visceral fat type obesity", "decreasing visceral fat" and "preventing visceral fat accumulation" and the like are exemplified as the same means with the aforementioned term "inhibiting visceral fat accumulation" in the present invention.

In addition, the food or drink of the present invention is useful for improving or preventing diseases caused by visceral fat accumulation, such as abnormal lipid metabolism and cardiovascular diseases typified by hyperlipidemia. Furthermore, the food or drink of the present invention can also be used for preventing the onset of metabolic syndrome, visceral fat type obesity and the like. Further, the food or drink of the present invention can treat or prevent various diseases, complications and the like caused by visceral fat accumulation, and can decrease the risks of those diseases, complications and the like, as same as mentioned above for the agent of the present invention.

The food or drink of the present invention is preferably marketed as food or drink attached with an indication that the food or drink is used for inhibiting visceral fat accumulation, for example, "food or drink containing a compound having an effect of inhibiting visceral fat accumulation indicated as 'For inhibiting visceral fat accumulation'" or "food or drink containing a plant extract indicated as 'For inhibiting visceral fat accumulation'" and the like. In addition, because the compound of the present invention, and a composition containing the same have an effect of inhibiting visceral fat accumulation, the indication of "inhibiting visceral fat accumulation" for the food or drink is thus considered to have a meaning of "improving visceral fat type obesity". Therefore, the food or drink of the present invention can be indicated as "For improving visceral fat type obesity". In other words, the indication of "For inhibiting visceral fat accumulation" may be replaced by the indication of "For improving visceral fat type obesity".

The wording used for such an indication as mentioned above is not necessarily be limited to the expression "For inhibiting visceral fat accumulation" or "For improving visceral fat type obesity", and any other wording expressing the effect for inhibiting visceral fat accumulation, or the effect for preventing and improving visceral fat type obesity of course falls within the scope of the present invention. As such a wording, for example, an indication based on various uses allowing consumers to recognize the effect for inhibiting visceral fat accumulation or the effect of improving visceral fat type obesity is also possible. Examples include indication of "Suitable for those who began to worry about waist size", "Suitable for those who tend to be visceral fat type obesity" and "Useful for decrease or elimination of risk factors (risks) of metabolic syndrome".

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth. The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, other documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

The present invention will be explained more specifically with reference to the following examples. However, the scope of the present invention is not limited to the following examples.

First of all, it is explained by Preparation Examples that the compound or composition of the present invention can be produced from a plant belonging to family Liliaceae.

Preparation Example 1

As examples of preparation from a plant belonging to family Liliaceae, examples of preparation of 3-O-β-D-glucopyranosyl-4-methylergost-7-en-3-ol from Aloe vera will be described below.

In an amount of 100 kg of mesophyll (clear gel portion) of *Aloe vera* was liquefied by using a homogenizer, added with 100 L of an ethyl acetate/butanol mixture (3:1) and stirred. The mixture was left overnight to separate the ethyl acetate/butanol mixture and the aqueous layer, and the ethyl acetate/butanol mixture was recovered. The extract from this ethyl acetate/butanol mixture obtained by concentrating the ethyl acetate/butanol mixture under reduced pressure weighed 13.5 g. The effect for inhibiting visceral fat accumulation was evaluated for the aforementioned aqueous layer by measurement of the mesenteric fat weight, and the extract from the ethyl acetate/butanol mixture in diabetes model mice described later in Reference Example 1, and the effect was observed for the extract from the ethyl acetate/butanol mixture. Therefore, it was attempted to isolate and purify components in the extract.

First, the aforementioned extract was examined by thin layer chromatography (Merck Ltd., Silica gel 60F254 and RP-18F2543). As a result, an isolation method based on normal phase silica gel column chromatography using a chloroform/methanol mixture appeared to be suitable. Accordingly, a solution of 13 g of the aforementioned extract dissolved in 1 mL of a chloroform/methanol mixture (1:1) was loaded on a column filled with 400 g of silica gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. The yields of crude purification products obtained from the fractions after removing the solvent were 1.44, 3.0, 1.17, 1.28 and 2.27 g, respectively. It was confirmed by the aforementioned evaluation of inhibiting visceral fat accumulation that, among these fractions, an active component existed in the fraction eluted with the mixture of chloroform:methanol=5:1 (crude purification product A).

Furthermore, to isolate and purify the active component from the aforementioned crude purification product A, this crude purification product A was examined by using thin layer chromatography (Merck Ltd., Silica gel 60F254 and RP-18F2543). As a result, an isolation method based on reverse phase silica gel column chromatography using methanol appeared to be suitable. Accordingly, the aforementioned crude purification product A was dissolved in 1 mL of a chloroform/methanol mixture (1:1) and loaded on a column filled with 180 g of COSMOSIL 140 (Nacalai Tesque, Inc.) to attain adsorption of the component to the column. Then, elution was performed by successively using 600 mL of 85% methanol solution, 600 mL of 95% methanol solution and 100 mL of 100% methanol. 3-O-β-D-glucopyranosyl-4-methylergost-7-en-3-ol was concentrated and isolated in a fraction eluted with 95% methanol and weighed 370 mg after removing the solvent. Hereafter, this product is referred to as compound 1.

Because the compound 1 showed an Rf value very close to that of β-sitosterol glucoside in an examination based on thin layer chromatography, it was anticipated to be a glycoside in which 1 molecule of sugar bound to the aglycon moiety. Furthermore, to examine the sugar composition of the compound 1, the compound 1 was subjected to methanolysis, then made into a TMS derivative and subjected to GC-MS measurement. As a result, in the measurement of the TMS derivative for the sugar portion of the compound 1, it showed main peaks at retention times of 14.28, 14.61 and 16.34 minutes, which were substantially consistent with the retention times of the main peaks of the sample glucose (Nacalai Tesque, Inc.), 14.27, 14.60 and 16.33 minutes. Furthermore, peaks corresponding to the main peaks of the sample galactose (Kishida Chemical Co., Ltd.) and the sample xylose (Kishida Chemical Co., Ltd.) were not observed. Thus, it was confirmed that the type of the sugar contained in the compound 1 was glucose.

From the above results, it was estimated that the compound 1 was a glycoside in which 1 molecule of glucose bound to the aglycon moiety. However, when the compound 1 was measured by $^{13}$C-NMR (125 MHz, CDCl$_3$), the existence of contaminants was confirmed. Therefore, it was considered that further purification should be required to determine its structure. Accordingly, the compound 1 was methanolyzed and then acetylated, and then the structure of the aglycon moiety as well as the binding site of the aglycon moiety and the sugar were confirmed. The method thereof will be described below.

In an amount of 50 mg of the compound 1 was dissolved in methanol (50 mL) containing 5% hydrochloric acid, and the solution was refluxed with heating for 6 hours for methanolysis and dried to obtain a residue (about 30 mg). This residue was purified by silica gel column chromatography (hexane:chloroform=9:1) to obtain a compound 2 (10 mg). This compound 2 (5 mg) was added with acetic anhydride and pyridine (2 drops each) and heated at 70° C. for 30 minutes for acetylation, and then the solvent of the reaction mixture was evaporated to obtain a compound 3. The analysis of the compound 3 was performed by GC-MS and $^{13}$C-NMR (125 MHz, CDCl$_3$).

The results of the analysis of this compound 3 by GC-MS and $^{13}$C-NMR (125 MHz, CDCl$_3$) are shown as follows. 3-acetoxy-4-methylergost-7-ene used as a reference substance was prepared by extracting from aloe, purifying the extract, confirming the structure of the purified product by $^{13}$C-NMR and acetylating the same.

[$^{13}$C-NMR spectrum (δ values, in CDCl$_3$)]; C-1:36.8, C-2: 27.3, C-3:78.7, C-4:37.0, C-5:46.9, C-6:26.8, C-7:117.4, C-8:139.4, C-9:49.7, C-10:34.9, C-11:21.6, C-12:39.7, C-13: 43.6, C-14:55.1, C-15:23.1, C-16:28.2, C-17:56.3, C-18: 12.0, C-19:14.2, C-20:36.5, C-21:19.0, C-22:33.9, C-23: 30.6, C-24:39.1, C-25:32.6, C-26:20.4, C-27:18.4, C-28: 15.6, C-29:15.3

[GC-MS]

Apparatus: GC-17A/GCMS5050A (SHIMADZU)

GC column: NEUTRA BOND-5 (GL Scienses)

Column temperature: 100° C. (2 min)→(10° C./min)→300° C. (28 min)

Injection temperature: 250° C.

Carrier gas: He (1.3 mL/min)

Interface temperature: 300° C.

MS mode: EI

Ionization energy: 70 eV

[Results]

Reference substance: 3-acetoxy-4-methylergost-7-ene: tR [min]=39.4; m/z 456 [M]$^+$, 441 [M-CH$_3$]$^+$, 396 [M-AcOH]$^+$, 381 [M-CH$_3$—AcOH]$^+$ Compound 3: tR [min]=39.2; m/z 456 [M]$^+$, 441 [M-CH$_3$]$^+$, 396 [M-AcOH]$^+$, 381 [M-CH$_3$—AcOH]$^+$ The results of the NMR measurement of the compound 3 were consistent with the values of 3-acetoxy-4-methylergost-7-ene shown in a literature (Yukagaku (Oil Chemistry), Vol. 36, No. 5, pp. 301-319, 1987). These results revealed that the compound 2 was 4-methylergost-7-en-3-ol. Furthermore, as a result of FAB-MS measurement, the molecular weight of the compound 1 was found to be 576. When the compound 2 (aglycon moiety) and glucose were condensed, the molecular weight of the obtained compound was 414 (compound 2)+180 (glucose)-18 (water)=576, which was consistent with the molecular weight of the compound 1. The above results revealed that the compound 1 had a structure of 3-O-β-D-glucopyranosyl-4-methylergost-7-en-3-ol.

The molecular formulas, molecular weights and chemical formulas of the compounds are shown below.

(Compound 1)

Molecular formula: C$_{35}$H$_{60}$O$_6$

Molecular weight: 576

Chemical formula: The following chemical formula (1)

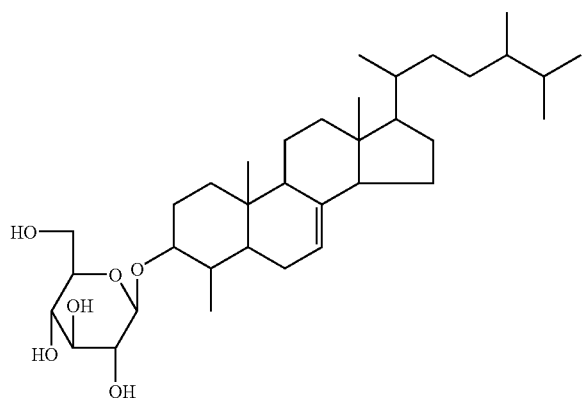

(1)

(Compound 2)

Molecular formula: C$_{29}$H$_{50}$O

Molecular weight: 414

Chemical formula: The following chemical formula (2)

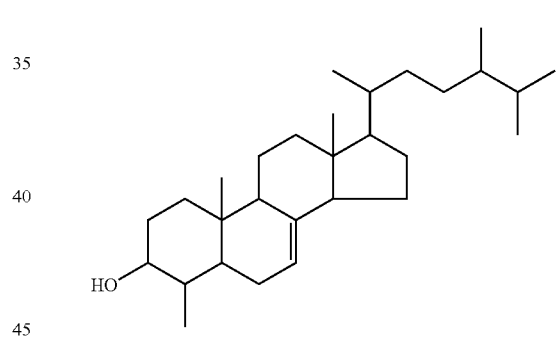

(2)

(Compound 3)

Molecular formula: C$_{31}$H$_{52}$O$_2$

Molecular weight: 456

Chemical formula: The following chemical formula (3)

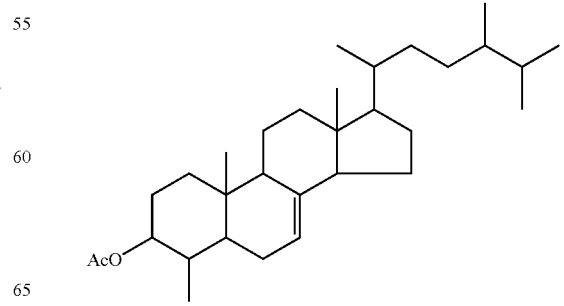

(3)

Preparation Example 2

Mesophyll (clear gel portion) of *Aloe vera* was dried by heating, 0.3 g of disrupted dry *Aloe vera* powder was added with 60 mL of 60, 80 or 100% ethanol, and the mixture was refluxed by heating at 60° C. for 1 hour. The extract was centrifuged at 1500 rpm for 20 minutes, and the supernatant was concentrated under reduced pressure to completely remove ethanol and thereby obtain a crude extract. The dry weights of the crude extracts obtained by extraction using 60, 80 and 100% ethanol were 65, 42 and 18 mg, respectively. It was confirmed by thin layer chromatography that these crude extracts contained 3-O-β-D-glucopyranosyl-4-methylergost-7-en-3-ol.

Preparation Example 3

Mesophyll (clear gel portion) of *Aloe vera* was dried by heating, 0.3 g of disrupted dry *Aloe vera* powder was added with 60 mL of water, and the mixture was refluxed by heating at 95° C. for 5 hours. The extract was centrifuged at 1500 rpm for 20 minutes, and the supernatant was lyophilized to obtain 75 mg of a crude extract. It was confirmed by thin layer chromatography that this crude extract contained 3-O-β-D-glucopyranosyl-4-methylergost-7-en-3-ol.

Preparation Example 4

Mesophyll (clear gel portion) of *Aloe vera* was dried by heating, disrupted and dried, 21 kg of *Aloe vera* powder thus prepared was added with 90 L of a chloroform/methanol mixture (2:1), then immersed overnight in the mixture at room temperature and collected by filtration, and the residue obtained by the filtration was added with 90 L of chloroform/methanol mixture (2:1) again. This procedure was repeated 4 times in total. The obtained filtrate (350 L) was concentrated at 28° C. to finally obtain 784 g of a crude extract. In an amount of 780 g of this crude extract was added with 2 L of a chloroform/methanol mixture (2:1), stirred for 1 hour and filtered to recover the chloroform/methanol mixture layer (A). The residue obtained by the filtration was successively added with 2.5 L of water and 2 L of ethyl acetate and stirred for 1 hour, and the ethyl acetate layer (B) was recovered. The remaining aqueous layer was added with 5 L of chloroform again and stirred for 1 hour, and the chloroform layer (C) was recovered.

The recovered organic solvent extracts A, B and C were mixed, concentrated at 23° C. and loaded on a silica gel column [glass column: 52 mm×350 mm, packed material: IR-63/210-W (Daiso Co., Ltd.)]. Subsequently, while monitoring the eluate by thin layer chromatography, 10 L of a hexane/chloroform mixture (1:1), 10 L of chloroform, 20 L of a chloroform/methanol mixture (10:1) and 20 L of a chloroform/methanol mixture (5:1) were passed through the column in this order, and a fraction 1 (about 1 L), fraction 2 (about 1.5 L), fraction 3 (about 1.5 L) and fraction 4 (about 1.5 L) were recovered in the order of the used elution solvents.

It was confirmed by thin layer chromatography that, among these, the fraction 3 contained the objective glycoside, and then the solvent of the fraction 3 was removed to obtain 131.6 g of a crude extract. In an amount of 130 g of this crude extract was loaded on a silica gel column [glass column: 70 mm×500 mm, packed material: SP-60-40/60 (Daiso Co., Ltd.)] again and eluted successively with 10 L of a chloroform/methanol mixture (30:1), 50 L of a chloroform/methanol mixture (20:1), 10 L of a chloroform/methanol mixture (10:1) and 10 L of a chloroform/methanol mixture (1:1) as elution solvents under conditions of a pressure of 10 kgf·cm$^{-2}$ and a flow rate of 40 mL/min. The eluates were fractionated as 100-mL fractions by using a fraction collector to collect fractions 1 to 8.

The collected fractions were examined by thin layer chromatography, and as a result, it was revealed that the objective glycoside and contaminants existed in the fraction 7. Therefore, this fraction was concentrated, loaded on a silica gel column [glass column: 70 mm×500 mm, packed material: SP-60-40/60 (Daiso Co., Ltd.)] again, and successively eluted with 10 L of a chloroform/methanol mixture (20:1) and 10 L of a chloroform/methanol mixture (10:1) as elution solvents under conditions of a pressure of 10 kgf·cm$^{-2}$ and a flow rate of 40 mL/min. As a result, 25.3 g of 3-O-β-D-glucopyranosyl-4-methylergost-7-en-3-ol was prepared, which was the objective glycoside contained in the fraction eluted with the chloroform/methanol mixture (10:1).

Example 1

This example was performed in order to evaluate an inhibitory effect of 3-O-β-D-glucopyranosyl-4-methylergost-7-en-3-ol and a squeezed liquid of *Aloe vera* on visceral fat accumulation by using ZDF (Zucker Diabetic Fatty) rats that are model animals for obese diabetes.

(1) Preparation of Sample

3-O-β-D-glucopyranosyl-4-methylergost-7-en-3-ol produced in Production Example 1 was used as a sample. The sample was dissolved in DMSO, and the concentration of the sample was adjusted with distilled water to 15 µg/ml and 1.5 µg/ml, to thereby prepare Test Samples A-1 and A-2, respectively. Meanwhile, a crude solution was obtained by crushing *Aloe vera* gel with a juicer, and then was subjected to filtration with a No. 200 mesh (manufactured by NBC), to thereby obtain a squeezed liquid of the Aloe vera gel as Test Sample B-1. The squeezed liquid of *Aloe vera* gel was diluted 20 folds to prepare Test Sample B-2. It was confirmed that the squeezed liquid of *Aloe vera* gel contained 0.1% of 3-O-β-D-glucopyranosyl-4-methylergost-7-en-3-ol by mass. In addition, final concentration of DMSO was adjusted to 0.2%. Further, a solution without the test samples was prepared as a negative sample.

(2) Test Method 6-week-old male ZDF rats (purchased from Charles River Laboratories, Inc., USA) were preliminarily fed with a high-fat diet (Research Diet, Inc.) for 1 month. These rats were divided into groups, each consisting of 6 rats. Each of the groups of rats was orally administered with 1 ml of solutions of the negative sample, Test Samples A-1, A-2, B-1 and B-2, respectively, per 400 g of body weight of a rat once a day successively for 44 days by using a sonde. In those cases, administration amounts of 3-O-β-D-glucopyranosyl-4-methylergost-7-en-3-ol of Test Samples A-1 and A-2 were 25 µg/kg and 2.5 µg/kg, respectively. In addition, administration amounts of *Aloe vera* solid content of Test Samples B-1 and B-2 were 2.5 g/kg and 0.125 g/kg, respectively.

On 45th day from the initiation of the administration, mesenteric fat weights were measured as the visceral fat.

Table 1 shows the mesenteric fat weights on the 45th day from the initiation of the administration. The mesenteric fat weights of the group administered with Test Samples A-1 (administration amount: 25 µg/kg) and A-2 (administration amount: 2.5 µg/kg) were 3.15±0.28 g and 4.99±0.53 g, respectively. As compared with a mesenteric fat weight of the group administered with the negative sample (6.83±1.10 g), it was observed that the mesenteric fat weights tend to decrease to 46.2% and 73.1% in the group administered with Test Samples A-1 and A-2. Therefore, it was confirmed that Test Samples A-1 and A-2 had statistically significant effects of inhibiting visceral fat accumulation. Furthermore, the mesenteric weights of the group administered with Test Samples B-1 (administration amount: 2.5 g/kg) and B-2 (administration amount: 0.125 g/kg) were 4.72±0.66 g and 4.75±0.79 g, respectively. As compared with a mesenteric fat weight of the group administered with the negative sample, it was observed that the mesenterium fat weights tend to decrease to 69.1% and 69.5% in the group administered with Test Samples B-1 and B-2. Therefore, it was confirmed that Test Samples B-1 and B-2 had statistically significant effects of inhibiting visceral fat accumulation. Furthermore, there was no side effects observed from pathologic viewpoints. In addition, p values in the tables indicate significance probability by Tukey-Kramer's test.

TABLE 1

| Sample | Mesenteric fat weight (g) | p value |
|---|---|---|
| Test Sample A-1 | 3.15 ± 0.28 * | 0.00003 |
| Test Sample A-2 | 4.99 ± 0.53 * | 0.007 |
| Test Sample B-1 | 4.72 ± 0.66 * | 0.0012 |
| Test Sample B-2 | 4.75 ± 0.79 * | 0.0039 |
| Negative sample | 6.83 ± 1.10 | — |

In the Table, "*" indicates that there was a statistically significant effect of inhibiting visceral fat accumulation.

Example 2

This example was performed in order to investigate an effect of 3-O-β-D-glucopyranosyl-4-methylergost-7-en-3-ol and a squeezed liquid of *Aloe vera* on an amount of food ingestion (amount of food consumption) and increase in body weight (amount of increased body weight) of rats.

(1) Preparation of Samples

3-O-β-D-glucopyranosyl-4-methylergost-7-en-3-ol produced in Production Example 1 was used as a sample. The sample was dissolved in DMSO, and the concentration of the sample was adjusted with distilled water to 10 μg/ml, to thereby prepare Test Sample C. Meanwhile, a crude solution was obtained by crushing *Aloe vera* gel with a juicer, and then was subjected to filtration with a No. 200 mesh (manufactured by NBC), to thereby obtain a squeezed liquid of the *Aloe vera* gel as Test Sample D. It was confirmed that the crush extract of *Aloe vera* gel contained 0.1% of 3-O-β-D-glucopyranosyl-4-methylergost-7-en-3-ol by mass. In addition, final concentration of DMSO was adjusted to 0.2%. Further, a solution without the test samples was prepared as a negative sample.

(2) Test Method 6-week-old male ZDF rats (purchased from Charles River Laboratories, Inc., USA) were preliminarily fed with a high-fat diet (Research Diet, Inc.) for 1 month. These rats were divided into groups, each consisting of 6 rats, after measuring their body weights. Each of the groups of rats was orally administered with 1 ml of solutions of Test Samples C, D and negative sample, respectively, per 400 g of body weight of a rat once a day successively for 44 days by using a sonde. In those cases, administration amounts of 3-O-β-D-glucopyranosyl-4-methylergost-7-en-3-ol of Test Sample C was 37.5 μg/kg. In addition, administration amounts of *Aloe vera* solid content of Test Samples D was 3.75 g/kg.

42 days after initiation of the administration, the body weights of the rats were measured, and differences between the body weights on the 42nd day and those measured before the initiation of the administration were regarded as amounts of increased body weights. In addition, weights of food consumed per day were measured once a week from the day of the initiation of the administration, and an average of the weights was regarded as an amount of food consumption per day.

(3) Test Results

Table 2 shows the amounts of food consumption per day and amounts of increased body weight during 42 days per rat.

It was observed that the groups administered with Test Samples C and D did not show significant increase or decrease in amount of food consumption as compared with the group administered with the negative sample. In addition, the amounts of increased body weight (increases in body weight) of the groups administered with Test Samples C and D were almost the same as that of the group administered with the negative sample. Therefore, it was revealed that 3-O-β-D-glucopyranosyl-4-methylergost-7-en-3-ol does not affect the amount of food ingestion and increase in body weight of rats.

TABLE 2

| Sample | Amount of food consumption (g) | Amount of increased body weight (g) |
|---|---|---|
| Test Sample C | 22.5 ± 1.2 | 166.5 ± 19.3 |
| Test Sample D | 21.7 ± 1.4 | 173.3 ± 32.5 |
| Negative sample | 22.5 ± 1.2 | 159.9 ± 37.2 |

INDUSTRIAL APPLICABILITY

According to the present invention, there can be provided an agent for inhibiting visceral fat accumulation, which is capable of maintaining a standard body weight without a reduction in body weight, and is effective for inhibiting progression of obesity without excessive diet restriction or the like, and a physiologically functional food or drink such as a food for specified health use containing the agent for inhibiting visceral fat accumulation. Thus, diseases, complications, and the like caused by the visceral fat accumulation, such as abnormal lipid metabolism and circulatory diseases can be ameliorated or prevented, and risks of those diseases, complications, and the like can also be reduced. In addition, the present invention also provides an effect of preventing onset of metabolic syndrome and lifestyle-related diseases which are indicated as risk factors of the metabolic syndrome, such as diabetes, hypertension, and hyperlipidemia.

What is claimed is:

1. A method of inhibiting visceral fat accumulation, comprising administering an isolated compound represented by the following chemical formula (1) to a target whose accumulation of visceral fat is to be inhibited;

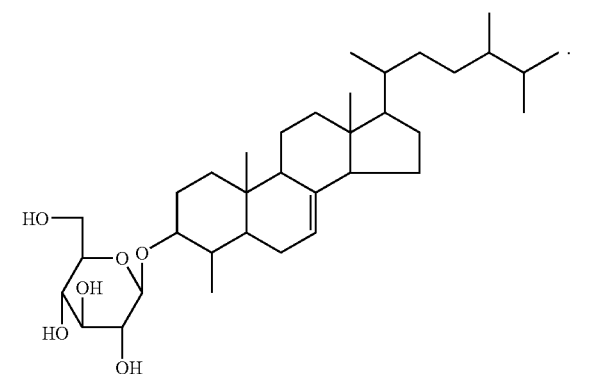

(1)

* * * * *